United States Patent
Delisle et al.

(10) Patent No.: US 12,024,538 B2
(45) Date of Patent: Jul. 2, 2024

(54) METHODS FOR REDUCING IMPURITIES IN SILK FIBROIN PREPARATIONS

(71) Applicant: COCOON BIOTECH INC., Mansfield, MA (US)

(72) Inventors: Scott Delisle, Mansfield, MA (US); Michael Santos, Mansfield, MA (US)

(73) Assignee: COCOON BIOTECH INC., Mansfield, MA (US)

( * ) Notice: Subject to any disclaimer, the term of this patent is extended or adjusted under 35 U.S.C. 154(b) by 0 days.

(21) Appl. No.: 18/481,313

(22) Filed: Oct. 5, 2023

(65) Prior Publication Data

US 2024/0025944 A1  Jan. 25, 2024

Related U.S. Application Data

(63) Continuation of application No. PCT/US2023/020655, filed on May 2, 2023.

(60) Provisional application No. 63/420,160, filed on Oct. 28, 2022, provisional application No. 63/337,325, filed on May 2, 2022.

(51) Int. Cl.
C07K 1/34 (2006.01)
C07K 1/36 (2006.01)
C07K 14/435 (2006.01)

(52) U.S. Cl.
CPC ............ *C07K 1/34* (2013.01); *C07K 1/36* (2013.01); *C07K 14/43586* (2013.01); *B01D 2315/16* (2013.01)

(58) Field of Classification Search
None
See application file for complete search history.

(56) References Cited

U.S. PATENT DOCUMENTS

| | | |
|---|---|---|
| 10,588,843 B2 | 3/2020 | Altman |
| 10,610,478 B2 | 4/2020 | Altman |
| 10,987,294 B2 | 4/2021 | Altman |
| 11,260,012 B2 | 3/2022 | Altman |
| 11,298,311 B2 | 4/2022 | Altman |
| 2016/0215030 A1* | 7/2016 | Bressner .......... C07K 14/43586 |
| 2019/0008923 A1 | 1/2019 | Kaplan |
| 2019/0127689 A1* | 5/2019 | Hu .......... C12N 5/0657 |
| 2020/0188268 A1 | 6/2020 | Altman |
| 2021/0138071 A1 | 5/2021 | Santos |
| 2021/0171573 A1 | 6/2021 | Arunkumar |
| 2021/0228684 A1 | 7/2021 | Delisle |
| 2022/0098234 A1 | 3/2022 | Susin Pires |
| 2022/0133615 A1 | 5/2022 | Altman |
| 2022/0331400 A1 | 10/2022 | Delisle |
| 2022/0372665 A1* | 11/2022 | Baryshyan ....... C07K 14/43586 |

FOREIGN PATENT DOCUMENTS

| | | | |
|---|---|---|---|
| CA | 3140673 A1 * | 12/2020 | .............. A61K 8/60 |
| CN | 113350574 A | 9/2021 | |
| WO | WO 2019/094702 A1 | 5/2019 | |
| WO | WO 2020/247594 A1 | 12/2020 | |

OTHER PUBLICATIONS

International Search Report and Written Opinion for PCT Application PCT/US2023/020655 dated Aug. 22, 2023.
Woltje, Michael, et al. A Fast and Reliable Process to Fabricate Regenerated Silk Fibroin Solution from Degummed Silk in 4 Hours, Int. J. Mol. Sci. 2021, 22, 10565.

* cited by examiner

*Primary Examiner* — Krishnan S Menon
(74) *Attorney, Agent, or Firm* — Karen A. LeCuyer; DeWitt LLP

(57) ABSTRACT

Described herein is a method of purifying a silk fibroin preparation including preparing an aqueous silk fibroin solution having a concentration of greater than or equal to 5% w/v silk fibroin from the silk fibroin preparation, wherein the silk fibroin preparation includes a chaotropic salt; and exchanging the chaotropic salt from the silk fibroin solution at a pH below the isoelectric point of the silk fibroin, wherein the pH is between 2 and 5, replacing the chaotropic salt with a buffer comprising 10 to 300 mM of a second salt, or a combination thereof, to prepare the purified silk fibroin.

13 Claims, No Drawings

METHODS FOR REDUCING IMPURITIES IN SILK FIBROIN PREPARATIONS

CROSS-REFERENCE TO RELATED APPLICATIONS

This application is a bypass continuation of PCT/US2023/20655, filed May 2, 2023, which claims priority to U.S. Provisional Applications 63/337,325 filed on May 2, 2022 and 63/420,160, filed on Oct. 28, 2022, which are incorporated herein by reference in their entirety.

BACKGROUND OF THE DISCLOSURE

Silk is a naturally occurring polymer. Most silk fibers are derived from silkworm moth (Bombyx mori) cocoons and include silk fibroin and sericin proteins. Silk fibroin is a fibrous material that forms a polymeric matrix bonded together with sericin. In nature, silk is formed from a concentrated solution of these proteins that are extruded through silkworm spinnerets to produce a highly insoluble fiber.

Many properties of silk fibroin make it an attractive candidate for products serving a variety of industries. Polymer strength and flexibility has supported classical uses of silk fibroin in textiles and materials, while silk fibroin biocompatibility has gained attention more recently for applications in the fields of medicine and agriculture. Additional uses for silk fibroin in applications related to material science are being explored as technologies for producing and processing silk fibroin advance.

Although a variety of products and uses related to silk fibroin are being developed, there remains a need for methods of producing and processing silk fibroin and formulations containing processed silk fibroin that can meet the demands. The present disclosure addresses these needs by providing methods for producing and processing silk fibroin as well as formulations of silk fibroin-based products useful in a variety of industries.

BRIEF SUMMARY

In an aspect, a method of purifying a silk fibroin preparation comprises preparing an aqueous silk fibroin solution having a concentration of greater than or equal to 5% w/v silk fibroin from the silk fibroin preparation, wherein the silk fibroin preparation comprises a chaotropic salt; and exchanging the chaotropic salt from the silk fibroin solution at a pH below the isoelectric point of the silk fibroin, wherein the pH is between 2 and 5, replacing the chaotropic salt with a buffer comprising 10 to 300 mM of a second salt, or a combination thereof, to prepare the purified silk fibroin.

DETAILED DESCRIPTION

Described herein are methods of reducing impurities, particularly elemental impurities introduced during purification, of silk fibroin preparations. During purification of silk fibroin which has been prepared by a process including dissolution in lithium bromide or another chaotropic salt as is standard in the art, the inventors have found that standard methods using tangential flow filtration (TFF) with water only in the retentate/replacement feed or dialysis provide a final material that has much higher lithium than bromide, typically 500-3000 ppm Li and 20-200 ppm Br, normalized to the amount of silk fibroin. This is unexpected, as it would be expected that both Li and Br would be completely or almost completely removed during exhaustive TFF or dialysis. In addition, as the mass of Br is 11.6 times greater than that of lithium one would expect that the Br residuals would be 11.6 times greater than Li, not 100-fold less.

For example, U.S. Pat. No. 9,517,191 and related patents claim that silk fibroin preparations have 0 ppm to 500 ppm of "inorganic residuals", such as lithium bromide residuals of 10 ppm to 300 ppm, "measurable using a high performance liquid chromatography lithium bromide assay". However, while Example 5 describes a TFF process to remove lithium bromide, the specification does not provide any data demonstrating removal of the lithium and bromide to the levels of 10 ppm to 300 ppm. Further, the '191 patent does not disclose if the level of inorganic residuals is normalized to the amount of silk fibroin in solution, which would be necessary. For example, any solution could be diluted with DI water to lower the level of residuals to below 300 ppm in solution but would not demonstrate any improved removal or residuals as compared to the amount of silk. Further, as shown in the examples herein, repeating the examples of the '191 patent provides a silk fibroin material with 1000-2000 ppm Li and 40-100 ppm Br, normalized to the amount of silk fibroin. The '191 patent does not provide a pH or salt composition for the TFF solution purported to remove Li and Br residuals.

The inventors have unexpectedly found that using a retentate having a pH of 3 to 4.5, such as pH 4, and/or using a TFF replacement feed solution of a salt concentration of 10 to 300 mM NaCl, for example, resulted in a dramatic decrease in Li levels, specifically ppm normalized to the amount of silk fibroin. The Br levels in these same samples can be 200-1500 ppm normalized to the amount silk fibroin. The reduction in Li levels is particularly important for product safety in pharmaceuticals and consumer products, for example. If one wanted to maintain the safe level of Li in a pharmaceutical product comprised of dried or concentrated silk fibroin in order to utilize the benefits of larger amounts of silk, these methods could be employed to ensure more complete removal of elemental impurities.

In an aspect, a method of purifying a silk fibroin preparation comprises preparing an aqueous silk fibroin solution having a concentration of greater than or equal to 5% w/v silk fibroin from the silk fibroin preparation, wherein the silk fibroin preparation comprises a chaotropic salt; and exchanging the chaotropic salt from the silk fibroin solution at a pH below the isoelectric point of the silk fibroin, wherein the pH is between 2 and 5, replacing the chaotropic salt with a buffer comprising 10 to 300 mM of a second salt, or a combination thereof, to prepare the purified silk fibroin.

Raw silk starting material can be obtained from the silkworm species *Bombyx mori*. Other examples of silk producer species include, but are not limited to, *Bombyx mandarina, Bombyx sinesis, Anaphe moloneyi, Anaphe panda, Anaphe reticulate, Anaphe ambrizia, Anaphe carteri, Anaphe venata, Anapha infracta, Antheraea assamensis, Antheraea assama, Antheraea mylitta, Antheraea pernyi, Antheraea yamamai, Antheraea polyphemus, Antheraea oculea, Anisota senatoria, Apis mellifera, Araneus diadematus, Araneus cavaticus, Automeris io, Atticus atlas, Copaxa multifenestrata, Coscinocera hercules, Callosamia promethea, Eupackardia calleta, Eurprosthenops australis, Gonometa postica, Gonometa rufobrunnea, Hyalophora cecropia, Hyalophora euryalus, Hyalophora gloveri, Miranda auretia, Nephila madagascarensis, Nephila clavipes, Pachypasa otus, Pachypasa atus, Philosamia ricini, Pinna squamosa, Rothschildia hesperis, Rothschildia lebeau, Sarnia Cynthia*, and *Sarnia ricini*.

In an aspect, the silk fibroin preparation comprises a chaotropic salt. As used herein, a chaotropic salt is a salt that disrupts the structure of macromolecules, such as silk fibroin.

In an aspect, the method comprises preparing an aqueous silk fibroin solution having a concentration of greater than or equal to 5% w/v silk fibroin from the silk fibroin preparation, wherein the silk fibroin preparation was prepared by a process comprising dissolving silk fibroin fibers in 5M to 13 M LiBr.

In an aspect, fibroin is produced by providing raw silk (e.g., unpurified silk such as silk yarn, cocoons), the raw silk comprising fibers containing silk fibroin and sericin. First, the raw silk is degummed in a salt solution, specifically a sodium carbonate solution with a sodium carbonate concentration of 0.05 to 1 M, specifically 0.1 to 1 M, more specifically 0.2 to 0.5 M sodium carbonate at a temperature of about 60 to about 90° C., and for a time of greater than 60 minutes to about 480 minutes. In a preferred aspect, degumming is performed in 0.5 M sodium carbonate at 85° C. for either 240 or 360 minutes. In an aspect, degumming provides degummed silk fibers having a sericin concentration of 0-0.5 wt %.

Of particular relevance to the present application, most prior art processes for purifying silk fibroin use 0.02 M sodium carbonate with boiling for 30 or 60 minutes to provide degummed silk fibroin. The inventors have found that this prior art process produces a material that is not favorable for subsequent processing steps, specifically TFF performed with a concentration of 5 to 20% w/v silk fibroin fibers. The prior art degumming process provides silk fibroin that is so viscous in solution it cannot be run at concentrations higher than about 1% w/v by TFF. Without being held to theory, it is believed that the molecular weight, polydispersity, and/or distribution of molecular weights of silk fibroin produced by prior art degumming processes is unfavorable for subsequent processing steps.

After the degumming, the silk fibroin fibers are further processed by dissolving, preferably in an aqueous solution comprising a chaotropic agent. Exemplary chaotropic agents include lithium bromide, lithium chloride, calcium chloride, ethanol, guanidinium chloride, and urea. Dissolving preferably includes using 5M to 13M lithium bromide for 1 hour to overnight at 50° C. to 100° C. to provide dissolved silk fibers, or dissolving the degummed silk fibers using a mixture of calcium chloride, ethanol, and water in a molar ratio of 1:2:8, respectively, for 1 hour to overnight at 50° C. to 100° C. to provide dissolved silk fibers. In a specific aspect, 10 wt % to 20 wt % silk fibroin is dissolved in 9.3M lithium bromide at 80° C. for 16 hours (overnight). In an aspect, using the TFF/Dialysis methods described herein the purified silk fibroin preparation comprises 10 to 600 ppm lithium per mg silk. In another aspect, the purified silk fibroin preparation comprises 10 to 600 ppm bromine per mass of silk fibroin.

In another aspect, the silk fibroin preparation is prepared by a process comprising dissolving the degummed silk fibers using a mixture of calcium chloride, ethanol, and water in a molar ratio of 1:2:8 for 1 hour to overnight at 50° C. to 100° C.

After the silk fibroin fibers are dissolved, they can be diluted prior to further purification. In an aspect, the dissolved silk fibers are diluted in water to provide a concentration of 5 to 20% w/v silk fibroin fibers. Optionally the diluted fibroin solution is filtered through a polypropylene, polyethersulfone, nylon, or cellulose, diatomaceous earth, perlite depth prefilter to remove particulates and provide a clarified silk fiber solution.

The aqueous silk fibroin solution having a concentration of greater than or equal to 5% w/v silk fibroin is then purified by and exchanging the chaotropic salt from the silk fibroin solution at a pH below the isoelectric point of the silk fibroin, wherein the pH is between 2 and 5, replacing the chaotropic salt with a buffer comprising 10 to 300 mM of a second salt, or a combination thereof, to prepare the purified silk fibroin.

In an aspect, the diluted silk fibroin fibers are then purified by tangential flow filtration (TFF) using, for example, continuous diafiltration by tangential flow filtration (TFF). Diafiltration is the fractionation process that washes smaller molecules through a membrane and leaves larger molecules in the retentate without significantly changing concentration. It can be used to remove salts or exchange buffers. It can remove ethanol or other small solvents or additives.

In continuous diafiltration, the diafiltration solution (water, buffer, or a salt solution) is added to the sample feed reservoir at the same rate as filtrate is generated. In this way the volume in the sample reservoir remains constant, but the small molecules (e.g., salts) that can freely permeate through the membrane are washed away in the filtrate (also called the permeate). Using salt removal as an example, each additional diafiltration volume (DV; also referred to herein as a diavolume) reduces the salt concentration further as the salt ions are removed in the filtrate. (A diafiltration volume is the volume of sample before the diafiltration solution is added.) Anything that isn't filtered out is the "retentate". In the present case, the retentate includes the majority of the silk fibroin.

In the process described herein, in one method, the "sample", also called the retentate, which includes the silk fibroin, is pH adjusted down to pH 2 to 5, for example, from its original pH of 8.5-9.

In an aspect, exchanging salt ions from the aqueous silk fibroin solution is by continuous diafiltration by tangential flow filtration (TFF) with a 5 kDa to 10 kDa molecular weight cut-off membrane by a process comprising providing a reduced pH retentate and filtering with at least three diafiltration volumes with a replacement feed of water, wherein the reduced pH retentate is a retentate comprising the silk fibroin and having a pH of 2 to 5. In an aspect, prior to providing the reduced pH retentate, the method comprises filtering least 3 diafiltration volumes, preferably at least 5 diafiltration volumes, with a water replacement feed.

The reduced pH retentate is a retentate comprising the silk fibroin and having a pH of 2 to 5, preferably 3 to 4.5, more preferably 3 to 4, and most preferably 4.

In another aspect, exchanging salt ions from the aqueous silk fibroin solution is by dialysis against the buffer having a pH of 2-5, wherein a pH of 2-5 is maintained through at least a portion of the dialysis procedure, preferably through the entire dialysis procedure.

In yet a further aspect, exchanging salt ions from the aqueous silk fibroin solution is by continuous diafiltration by tangential flow filtration (TFF) with a 5 kDa to 10 kDa molecular weight cut-off membrane by a process comprising filtering with at least three diafiltration volumes of a salt solution replacement feed, wherein the salt solution replacement feed comprises 10 to 300 mM of the salt. In an aspect, prior providing the salt solution replacement feed, the method comprises filtering least 3 diafiltration volumes, preferably at least 5 diafiltration volumes, with a water replacement feed.

In an aspect, the salt solution replacement feed, e.g., the second salt, comprises 10 to 300 mM of a Mg, Ca, K, or Na salt, specifically NaCl or CaCl$_2$, more specifically 150 mM NaCl. The pH of the salt solution replacement is not critical, but is preferably unbuffered, such as between pH 6 and 8.

In another aspect, exchanging salt ions from the aqueous silk fibroin solution is by dialysis in the buffer comprising 10 to 300 mM of the monovalent or divalent salt.

In another aspect, the method further comprises adjusting the pH of the purified silk fibroin preparation to a pH of 7-9, preferably 8.5-9.

In the following aspects, the silk fibroin preparation is prepared by a process comprising dissolving the degummed silk fibers using a mixture of calcium chloride, ethanol, and water in a molar ratio of 1:2:8 for 1 hour to overnight at 50° C. to 100° C.

In an aspect, exchanging salt ions comprises continuous diafiltration by tangential flow filtration (TFF), dialysis, or a combination thereof. In an aspect, the calcium ions are reduced to 10 to 500 ppm.

In this case, exchanging salt ions from the aqueous silk fibroin solution is by tangential flow filtration (TFF) with a 5 kDa to 10 kDa molecular weight cut-off membrane by a process comprising providing a reduced pH retentate and filtering with at least three diafiltration volumes with a replacement feed of water, wherein the reduced pH retentate is a retentate comprising the silk fibroin and having a pH of 2 to 5.

Alternatively, purifying the silk fibroin solution is by dialysis in the buffer having a pH of 2-5, wherein a pH of 2-5 is maintained through at least a portion of the dialysis procedure, preferably through the entire dialysis procedure.

In another alternative, exchanging salt ions from the aqueous silk fibroin solution is by continuous diafiltration by tangential flow filtration (TFF) with a 5 kDa to 10 kDa molecular weight cut-off membrane by a process comprising filtering with at least three diafiltration volumes of a salt solution replacement feed, wherein the salt solution replacement feed comprises 10 to 300 mM of the monovalent or divalent salt.

In yet another alternative, exchanging salt ions from the aqueous silk fibroin solution is by dialysis in the buffer comprising 10 to 300 mM of the salt.

In any of the foregoing aspects, the silk fibroin preparation is prepared by degumming silk yarn in 0.05 to 1 M sodium carbonate at a temperature of about 60° C. to about 90° C., and for a time of greater than 60 minutes to about 480 minutes, to provide degummed silk fibers having a sericin concentration of 0-0.5 wt %.

Following TFF, the solution may be filtered through a ~0.8-2 µm polypropylene, polyethersulfone, nylon, or cellulose, diatomaceous earth, perlite depth filter and stored at either frozen to –80° C. or stored at 4° C., preferably at a silk fibroin concentration of 5% to 20% (w/v).

The silk fibroin prepared by the foregoing method preferably has a weight average molecular weight of less than 90 kDa or less than as measured by size exclusion chromatography depending upon the method used, or less than 20 kDa as determined by dynamic light scattering. It is important to note that the determined molecular weight of silk fibroin preparations is highly dependent upon the method used to determine molecular weight. The silk fibroin prepared by the foregoing method also preferably has polydispersity of less than 1.4 as determined by dynamic light scattering.

The silk fibroin preparations disclosed herein can be used in a therapeutic application, an agricultural application, and/or a material science application, for example. The SBP may be used in a therapeutic application, wherein the SBP includes or is combined with one or more of: (a) a pharmaceutical composition, (b) an implant, (c) a coating, (d) a food or health supplement., or (e) device, the pharmaceutical composition, implant, coating, supplement or device optionally including one or more of: (i) an excipient, and (ii) a therapeutic agent. An agricultural composition comprising silk fibroin may also include a fertilizer, a nutrient, an agricultural product, a pesticide, an insecticide, an herbicide, and anti-fungal, and the like. In materials science applications, the silk fibroin may be combined with a) an adhesive; (b) a biomaterial; (c) a coating; (d) a conductor; (e) a composting agent; (f) a cosmetic, (g) an emulsifier; (h) an excipient, i) a fiber; (j) a film; (k) a filter; (l) a food product or additive; (m) an insulator; (n) a lubricant; (o) a membrane; (p) a metal or metal replacement; (q) a microneedle; (r) a nanomaterial; (s) a particle; (t) a paper additive; (u) a plastic or plastic replacement; (v) a polymer; (w) a sensor; (x) a textile; and/or (y) a thickening agent.

Examples of cosmetics include, but are not limited to, shampoos, conditioners, lotions, foundations, concealers, eye shadows, powders, lipsticks, lip glosses, ointments, mascara, gels, sprays, eye liners, liquids, solids, eyebrow mascaras, eyebrow gels, hairspray, moisturizers, dyes, minerals, perfumes, colognes, rouges, natural cosmetics, synthetic cosmetics, soaps, cleansers, deodorants, creams, towelettes, bath oils, bath salts, body butters, nail polish, hand sanitizer, primers, plumpers, balms, contour powders, bronzers, setting sprays, and setting powders.

As used herein, the term "consumer products" refers to goods or merchandise purchasable by the public. Consumer products may include, but are not limited to, agricultural products, therapeutic products, veterinary products, and products for household use. Non-limiting examples of consumer products include cleaning supplies, sponges, brushes, cloths, protectors, sealant, adhesives, lubricants, protectants, labels, paint, clothing, insulators, devices, bandages, screens, electronics, batteries, surfactants, synthetic clothing, laundry pods or tablets, dishwasher pods or tablets, glitter, disposable cups, disposable plates, disposable silverware (e.g. forks, knives, spoons), wet wipes, tires, tennis balls, glitter, cigarette butts, tea bags, and paint.

The invention is further illustrated by the following examples.

EXAMPLES

Comparative Example 1: DSC-SC-05-01 Processing (Degumming and Desalting as in Rockwood et al., Nature Protocols, 6, pp. 1612-1631, 2011)

Silk fibroin was prepared by degumming silk cocoons in a sodium carbonate solution, dissolving in lithium bromide, and purifying via dialysis. First, for degumming, 3 L of DI water and 6.4 g of sodium carbonate were added to a 4 L beaker and stirred until dissolved and homogeneous (0.02 M sodium carbonate). This solution was covered with foil and brought to a rolling boil. 7.5 g of silk cocoons cut into small pieces was added. The cocoons were then degummed for 30 minutes while boiling with periodic agitation. After 30 minutes, the silk was removed and rinsed under cold running water. It was then rinsed in 1.5 L of DI water with stirring for 20 minutes with two exchanges (3 total rinses). The silk was then squeezed until all water was removed, stretched out, and placed on foil to dry in a room temperature fume hood overnight.

After drying, 5.4 g of the silk fibroin was packed into a 100 mL beaker and 21.6 mL of 9.3 M lithium bromide was added. The beaker was covered with foil and allowed to heat at 60° C. for 4 hours. The resulting 20% (w/v) silk fibroin solution in lithium bromide was then poured into 3.5 kDa dialysis cassettes and placed into 5 L of DI water under stirring to dialyze. The water was completely exchanged 6 times over the next 48 hours. After dialysis, the solution was combined, centrifuged for 20 minutes at 10000×g to remove any insoluble particulates, and stored at 4° C. prior to analysis.

Comparative Example 2: DSC-SC-05-02 Processing (Degumming and Desalting as in Rockwood et al.)

Silk fibroin was prepared using the method of Comparative Example 1, except degumming was done by boiling for 60 minutes.

Comparative Example 3: DSC-SC-06-01 Processing (Degumming and Desalting as in U.S. Pat. No. 9,517,191)

Silk fibroin was prepared by degumming silk cocoons in a sodium carbonate solution, dissolving in lithium bromide, and purifying via dialysis. First, 1 L of DI water and 2.1 g of sodium carbonate were added to a 2 L beaker and stirred until dissolved and homogeneous (0.02 M sodium carbonate). This solution was covered with foil and brought to a rolling boil. 10 g of silk cocoons cut into small pieces was added. The cocoons were then degummed for 30 minutes while boiling with periodic agitation. After 30 minutes, the silk was immediately removed and placed in 1 L of DI water heated to 60° C. for 20 minutes. It was then removed and rinsed under cold running water. The silk was then squeezed until all water was removed, stretched out, and placed on foil to dry in a room temperature fume hood overnight.

After drying, 7.2 g of the silk fibroin was packed into a 100 mL beaker and 28.8 mL of 9.3 M lithium bromide was added. The beaker was covered with foil and allowed to heat at 100° C. for 1 hour. The resulting 20% (w/v) silk fibroin solution in lithium bromide was then poured into 3.5 kDa dialysis cassettes and placed into 5 L of DI water under stirring to dialyze. The water was completely exchanged 6 times over the next 48 hours. After dialysis, the solution was combined, centrifuged for 20 minutes at 10000×g to remove any insoluble particulates, and stored at 4° C. prior to analysis.

Comparative Example 4: DSC-SC-06-02 Processing (Degumming and Desalting as in U.S. Pat. No. 9,517,191)

Silk fibroin was prepared by the same method of Comparative Example 3 except degumming was done by boiling for 60 minutes.

Comparative Example 5: DSC-SC-07 Processing (Degumming Similar to WO 2020/247594, Example 34; Desalting as in Rockwood et al.)

Silk fibroin was prepared by degumming silk yarn in a sodium carbonate solution, dissolving in lithium bromide, and purifying via dialysis. Silk fibroin was prepared by degumming silk yarn in a sodium carbonate solution, dissolution in lithium bromide and purification via tangential flow filtration. 31.3 L of water and 1.66 kg of sodium carbonate (0.5 M sodium carbonate) were added to a vessel and heated to 85° C. 2.5 kg of silk yarn was added to the solution. The silk yarn was degummed for 4 hours at 85° C. After 4 hours, the silk yarn was removed and rinsed under DI water to remove excess carbonate solution. The fibroin fibers were then squeezed to remove water and spread in a 60° C. oven to dry over two days.

After drying, 7.5 g of the silk fibroin was packed into a 100 mL beaker and 30 mL of 9.3 M lithium bromide was added. The beaker was covered with foil and allowed to heat at 60° C. overnight (around 20 hours). The resulting 20% (w/v) silk fibroin solution in lithium bromide was then poured into 3.5 kDa dialysis cassettes and placed into 5 L of DI water under stirring to dialyze. The water was completely exchanged 6 times over the next 48 hours. After dialysis, the solution was combined, centrifuged for 20 minutes at 10000×g to remove any insoluble particulates, and stored at 4° C. prior to analysis.

Comparative Example 6: TF-124 Processing: (Degumming and Desalting Similar to WO 2020/247594 Example 34)

Silk fibroin (SF) was prepared by first degumming silk yarn in a sodium carbonate solution. 31.3 L of water and 1.66 kg of sodium carbonate (0.5 M sodium carbonate) were added to a vessel and heated to 85° C. 2.5 kg of silk yarn was added to the solution. The silk yarn was degummed for 4 hours at 85° C. After 4 hours, the SF yarn was removed and rinsed under DI water to remove excess carbonate solution. The SF fibers were then squeezed to remove water and spread in a 60° C. oven to dry over two days.

To dissolve the degummed SF fibers, 280 g of the degummed SF was placed in a 1-gallon glass jar along with 1.74 kg of 9.3 M lithium bromide solution. The jar was incubated at 60° C. overnight to dissolve the SF fibers. Prior to tangential flow filtration, the silk fibroin solution was diluted from 20% (w/v) SF to 5% (w/v) SF with DI water. The diluted solution was then filtered through an approximately 5 µm cellulose membrane to remove any remaining particulates.

A tangential flow filtration (TFF) system with a single 1.14 $m^2$ Pellicon® 3 cassette with an Ultracel® 5 kDa membrane was used for removal of lithium bromide. Prior to introduction of SF to the system, the system was washed with DI water and sanitized with 0.1 N sodium hydroxide. The system was then flushed with water to remove sodium hydroxide.

Using the TFF system, the solution was concentrated from 5% (w/v) to 10% (w/v) SF. Continuous (or constant volume) diafiltration was performed with the 10% (w/v) SF to remove lithium bromide. The silk fibroin and lithium bromide solution was diafiltered for 10 diavolumes with a replacement feed of DI water. Permeate flux was measured every half-diavolume as liters per $m^2$ of membrane surface area per hour. The solution was then concentrated to half of its diafiltration volume and collected. Following TFF, the solution was filtered through an approximately 1 µm cellulose filter and stored at 4° C. until elemental analysis was completed.

Inventive Example 7: TF-122 Processing

SF was first degummed and dissolved as in Example 6 except that 283 g of degummed SF was placed in a 1-gallon glass jar along with 1.82 kg of 9.3 M lithium bromide solution. The TFF system was the same as in Example 6.

Continuous diafiltration was performed at 10% (w/v) SF to remove lithium bromide. The silk fibroin was diafiltered for 7 diavolumes with a replacement feed of 150 mM sodium chloride solution in water. The solution was then concentrated to half of its diafiltration volume and collected. Following TFF, the solution was filtered through an approximately 1 μm cellulose filter and stored at 4° C. until elemental analysis was completed.

Inventive Example 8: TF-123 Processing

SF was first degummed and dissolved as in Example 6 except that 283 g of degummed SF was placed in a 1-gallon glass jar along with 1.82 kg of 9.3 M lithium bromide solution. The TFF system was the same as in Example 6.

The silk fibroin and lithium bromide solution was first adjusted to pH 4 with hydrochloric acid. Using the TFF system, the solution was concentrated from 5% (w/v) to 10% (w/v) SF while maintaining a pH of 4. Continuous diafiltration was performed at 10% (w/v) SF to remove lithium bromide. The silk fibroin was diafiltered for 7 diavolumes with a replacement feed of DI water while maintaining a pH of 4. The solution was then concentrated to half of its diafiltration volume and collected. The silk fibroin solution was then quickly adjusted to between pH 8.5 and 9.0 using sodium hydroxide. The solution was filtered through an approximately 1 μm cellulose filter and stored at 4° C. until elemental analysis was completed.

Inventive Example 9: TF-125 Processing

SF was first degummed and dissolved as in Example 6. The TFF system was the same as in Example 6.

Using the TFF system, the solution was concentrated from 5% (w/v) to 10% (w/v) SF. Continuous diafiltration was performed at 10% (w/v) SF to remove lithium bromide. The silk fibroin was diafiltered for a total of 10 diavolumes with a replacement feed of DI water. After the fifth diavolume, the silk fibroin feed solution was quickly adjusted to pH 4 using hydrochloric acid. The remaining diavolumes were completed while maintaining a pH of 4. The solution was then concentrated to half of its diafiltration volume and collected. Following TFF, the solution was adjusted back to a pH between 8.5 and 9.0 using sodium hydroxide and filtered through an approximately 1 μm cellulose filter and stored at 4° C. until elemental analysis was completed.

Inventive Example 10: TF-126 Processing

SF was first degummed and dissolved as in Example 6. The TFF system was the same as in Example 6.

Using the TFF system, the solution was concentrated from 5% (w/v) to 10% (w/v) SF. Continuous diafiltration was performed at 10% (w/v) SF to remove lithium bromide. The silk fibroin was first diafiltered for 5 diavolumes with a replacement feed of DI water. The silk fibroin was then diafiltered for 5 additional diavolumes with a replacement feed of 150 mM sodium chloride solution, for a total of 10 diavolumes. The solution was then concentrated to half of its diafiltration volume and collected. Following TFF, the solution was filtered through an approximately 1 μm cellulose filter and stored at 4° C. until elemental analysis was completed.

Inventive Example 11: TF-127 Processing

SF was first degummed and dissolved as in Example 6. The TFF system was the same as in Example 6.

The silk fibroin and lithium bromide solution was first adjusted to pH 4 with hydrochloric acid. Using the TFF system, the solution was concentrated from 5% (w/v) to 10% (w/v) SF while maintaining a pH of 4. Continuous diafiltration was performed at 10% (w/v) SF to remove lithium bromide. The silk fibroin was diafiltered for 10 diavolumes with a replacement feed of DI water. The silk fibroin and lithium bromide solution was maintained at pH 4 for the first five diavolumes. After the fifth diavolume, the silk fibroin solution was quickly adjusted to between pH 8.5 and 9.0 using sodium hydroxide. The silk fibroin was then diafiltered for the final 5 diavolumes. The solution was then concentrated to half of its diafiltration volume and collected. Following TFF, the solution was filtered through an approximately 1 μm cellulose filter and stored at 4° C. until elemental analysis was completed.

Inventive Example 12: TF-128 Processing

SF was first degummed and dissolved as in Example 6. The TFF system was the same as in Example 6.

Using the TFF system, the solution was concentrated from 5% (w/v) to 10% (w/v) SF. Continuous diafiltration was performed at 10% (w/v) SF to remove lithium bromide. The silk fibroin was first diafiltered for 5 diavolumes with a replacement feed of 150 mM sodium chloride solution in water. The silk fibroin was then diafiltered for 5 additional diavolumes with a replacement feed DI water. The solution was then concentrated to half of its diafiltration volume and collected. Following TFF, the solution was filtered through a an approximately 1 μm cellulose filter and stored at 4° C. until elemental analysis was completed.

Inventive Example 13: TF-129 Processing

SF was first degummed and dissolved as in Example 6. The TFF system was the same as in Example 6.

Using the TFF system, the solution was concentrated from 5% (w/v) to 10% (w/v) SF. Continuous diafiltration was performed at 10% (w/v) SF to remove lithium bromide. The silk fibroin was diafiltered for 10 diavolumes total with a replacement feed of DI water. After the third diavolume, the silk fibroin solution was quickly adjusted to pH 4 using hydrochloric acid. The silk fibroin was diafiltered for 4 diavolumes while maintaining a pH of 4. After the seventh diavolume, the silk fibroin solution was quickly adjusted to between pH 8.5 and 9.0 using sodium hydroxide. The silk fibroin was then diafiltered for the final 3 diavolumes. The solution was then concentrated to half of its diafiltration volume and collected. Following TFF, the solution was filtered through an approximately 1 μm cellulose filter and stored at 4° C. until elemental analysis was completed.

Results: Elemental Analysis of Samples Prepared in Comparative Examples 1-6 and Inventive Examples 7-13

Elemental analysis was performed on the samples. The method for determining bromine consists of the following: 0.10-0.15 gram aliquots of silk fibroin samples in solution are weighed out into 40 mL centrifuge tubes. 1 mL of Tetra-methyl ammonium hydroxide (TMAH) is added, and the sample is heated at 90 C overnight. After the samples have cooled to room temperature, 24 mL of DI water is added, and the samples are shaken for 1 hour before analysis via Inductively Coupled Plasma-Mass Spectrometry (ICP-MS).

The method for determining lithium consists of: 1 mL aliquots of silk fibroin samples in solution are weighed into Teflon digestion tubes. 2 mL of 2% nitric acid is added and the solution is allowed to react. An additional 2 mL of 0.5% perchloric acid is then added and the tube is heated to 180 C to evaporate off the nitric acid and complete the digestion. The solution is then diluted to 20 mL final with the addition of DI water. The sample is then diluted 10-fold with DI water and analyzed via ICP-MS. Ion levels were quantified via standard curves for each element.

Elemental levels for each batch were then normalized to the amount of silk fibroin in solution in each sample and reported as ppm lithium or bromine per silk fibroin (or mg Li or Br per kg silk fibroin). The results are represented in the following tables. Also below are the flux results and detailed descriptions of the pH and conductivity values of the silk fibroin and lithium bromide feed solutions for the TFF processes run in Examples 6 and 9-13.

Table 1 shows the elemental analysis data summary.

TABLE 1

ELEMENTAL ANALYSIS DATA SUMMARY

| Sample | TFF Replacement Feed | Lithium ppm (mg Li/kg silk fibroin) | Bromine ppm (mg Br/kg silk fibroin) | Total ppm residuals | Mass Ratio Li:Br |
|---|---|---|---|---|---|
| Comparative Example 1 | NA, dialysis | 741 | 72 | 813 | 10.3 |
| Comparative Example 2 | NA, dialysis | 830 | 104 | 934 | 8.0 |
| Comparative Example 3 | NA, dialysis | 1043 | 97 | 1140 | 10.8 |
| Comparative Example 4 | NA, dialysis | 1329 | 50 | 1379 | 26.6 |
| Comparative Example 5 | NA, dialysis | 2530 | 24 | 2554 | 105.4 |
| Comparative Example 6 | DI water for diavolumes 1-10 | 1740 | 71 | 1811 | 24.5 |
| Inventive Example 7 | 150 mM sodium chloride for diavolumes 1-7 | 325 | 1346 | 1671 | 0.2 |
| Inventive Example 10 | DI water for diavolumes 1-5, 150 mM sodium chloride for diavolumes 6-10 | 48 | 313 | 361 | 0.2 |
| Inventive Example 12 | 150 mM sodium chloride for diavolumes 1-5, DI water for diavolumes 6-10 | 296 | 124 | 420 | 2.4 |
| Inventive Example 8 | DI water for diavolumes 1-7, silk solution adjusted to pH 4, pH maintained at 4 | 94 | 1436 | 1530 | 0.1 |
| Inventive Example 9 | DI water for diavolumes 1-10, silk solution adjusted to pH 4 and maintained at 4 in diavolumes 6-10 | 28 | 53 | 81 | 0.5 |
| Inventive Example 11 | DI water for diavolumes 1-10, silk solution adjusted to pH 4, pH maintained a4 for diavolumes 1-5, then pH 8.5 to 9 for diavolumes 6-10 | 585 | 23 | 608 | 25.4 |
| Inventive Example 13 | DI water for diavolumes 1-10, silk solution adjusted to pH 4 and maintained at 4 for diavolumes 4-7 | 189 | 23 | 212 | 8.2 |

As shown in Table 1, the different methods used in these TFF runs lead to significant variation in the amounts of lithium and bromine in the resulting silk fibroin solution. Comparative Examples 1-5 all use dialysis for desalting. Each of Comparative Examples 1-5 has a lithium concentration, normalized in ppm per kg of silk fibroin) of 741-2530 ppm, with significantly lower bromine. Unexpectedly, not only does dialysis not remove the lithium and bromine, but retention of lithium over bromine is favored. Without being held to theory, it is believed that the charged state of the silk fibroin protein encourages binding and attraction towards the lithium ion, rendering it difficult or impossible to remove through passive or static dialysis, or even during continuous TFF. Only by altering the configuration of the silk protein or by encouraging an alternative thermodynamic state would it be possible to remove this lithium and ensure a more complete purity of the silk fibroin product. It is also notable that the preferential retention of lithium occurs whether degumming is done in 0.02 or 0.5 M sodium carbonate.

Comparative Example 6 is the method of degumming and desalting similar to WO 2020/247594 Example 34. Continuous TFF involves pumping the silk fibroin and lithium bromide solution against a semipermeable membrane, forcing out water, lithium ions, bromine ions, and a very small amount of silk fibroin that fits through the pores. The solution lost through the membrane (the permeate) is measured and replaced simultaneously as the run progresses.

This replacement feed is normally DI water as described in WO 2020/247594 Example 30. As shown in Table 1, performing TFF in water, similar to dialysis, resulted in preferential retention of lithium ions compared to bromine.

n Examples 7-13, degumming proceeded as in WO 2020/247594 Example 30, but the TFF was performed in salt solution or low pH instead of or in addition to water. Without being held to theory, the pH reduction method was chosen as a way to conformationally change the silk fibroin by bringing it below its isoelectric point, which is believed to expose, conformationally, some of the bound lithium and bromine for replacement. Also, without being held to theory, the salt replacement was chosen to potentially provide the silk fibroin a safer, more chemically attractive ion to bind to, forcing off any lingering lithium or bromine bound to the protein. It is also important to note that degumming according to Comparative Examples 1-4 provided a silk fibroin preparation that could not be processed by TFF at concentrations of 5-10% silk fibroin. Degumming at high sodium carbonate and low temperature allows for the TFF processes to proceed at high silk fibroin concentrations. Without being held to theory, it is believed that when the silk fibroin concentration is low, e.g., 1% w/v, the large volumes used to filter the same amount of silk fibroin lead to instability in the protein. In addition, use of 1% w/v silk fibroin can lead to instability evidenced by irreversible precipitation. Advantageously, performing TFF with 5-10% w/v silk fibroin eliminates many of the issues resulting from use of more dilute solutions.

Comparing the amount of lithium in the samples, as shown in Table 1, inventive methods (Examples 7-13) resulted in reduced lithium content compared to both a previous TFF method (Comparative Example 6) and Comparative Examples 1-5. Comparative Examples 1 and 2 were chosen as examples of the most common processing method for silk fibroin solution in the art. Comparative Examples 3 and 4 were chosen as examples of processes that specifically claim low levels of inorganic impurity (lithium and bromide) are produced. Comparative Example 5 was chosen to demonstrate that the desalting process is the significant part of the process regarding elemental impurity levels rather than the degumming step. All of these processes showed similar levels of lithium and bromide, with total impurity levels ranging from 813 to 2554 ppm normalized to the amount of silk fibroin.

Comparative Example 6 represents a TFF process as described previously. This process showed similar elemental impurity levels to Comparative Examples 1-5.

In Inventive Examples 7, 10 and 12, 150 mM sodium chloride was used in the TFF method. Examples 7 shows a decrease in lithium but a drastic increase in bromine compared to Example 6 (TFF with water only). Example 10 shows even more marked decrease in lithium and bromine compared to Example 7. This may be due to the 3 additional diavolumes of water/sodium chloride in these batches compared to Example 7. Example 12 represents the reverse of Example 10, where the changes are made in the first 5 diavolumes as opposed to the final 5 diavolumes. Thus, the ordering of diavolumes with replacement feeds of either water or salt solution can impact the final product.

In Inventive Examples 8, 9 11 and 13, reduced pH was used in the TFF method. Example 8 shows a decrease in lithium but a drastic increase in bromine compared to Example 6 (TFF with water only). pH change seems to be a more effective manner of reducing lithium than adding salt, but the total impurity content in both Examples 7 and 8 remains comparable to Example 6. But the ratio of lithium to bromide has changed drastically, with implications for safety and elemental binding of the silk fibroin.

Example 9 shows an even more marked decrease in lithium compared to Example 8. This may be due to the 3 additional diavolumes in these batches compared to Example 8. The pH change in the manner of Example 9 leads to a more complete elemental impurity reduction.

Example 11 represents the reverse of Example 9, where the changes are made in the first 5 diavolumes as opposed to the final 5 diavolumes. Example 11 shows only a decrease in lithium When the DI water replacement feed is implemented can thus be used to adjust the relative levels of lithium and bromine.

Example 13 demonstrates the reduction in lithium when a pH change is induced. Example 13 ran for 3 diavolumes at pH 8-9, then for 4 at pH 4, then finally for 3 more at pH 8-9 again. Example 11, for comparison, ran for 5 diavolumes at pH 4 and then 5 at pH 8-9. When, as in Example 13, the process involves diavolumes at pH 8-9 first, the lithium content is more effectively reduced. The bromine levels remain unchanged between the two, though the ratio of the two was clearly altered. Thus, in an optimized process, several diavolumes at an unadjusted pH are followed by several diavolumes at low pH, all with a replacement feed of water. The replacement feed of sodium chloride solution demonstrates some reduction in lithium with some increase in bromine, indicating usefulness in case pH alteration is not possible or if one is attempting to attach different combinations of ionic species to silk fibroin. The ability to alter the ratio of lithium to bromine indicates that this process can be tailored to a wide variety of desired ratios, and that other elements could be bound to silk fibroin as ionic species be being taken through this TFF process.

Table 2 shows pH values for silk fibroin and lithium bromide solutions during TFF processes.

TABLE 2

PH VALUES FOR SILK FIBROIN AND LITHIUM BROMIDE SOLUTIONS DURING TFF PROCESSES

| | Example 6 | Example 9 | Example 10 | Example 11 | Example 12 | Example 13 |
|---|---|---|---|---|---|---|
| pH at DV 3 | 8.6 | 8.6 | 8.6 | 4.1 | 8.5 | 8.7 |
| pH at DV 4 | 8.7 | 8.7 | 8.7 | 4 | 8.6 | 4 |
| pH at DV 5 | 8.7 | 8.7 | 8.7 | 4.1 | 8.6 | 4 |
| pH at DV 6 | 8.7 | 4 | 8.6 | 8.7 | 8.7 | 4 |
| pH at DV 7 | 8.7 | 4 | 8.6 | 8.6 | 8.7 | 4 |
| pH at DV 8 | 8.6 | 4 | 8.6 | 8.5 | 8.7 | 8.7 |
| pH at DV 9 | 8.6 | 4.1 | 8.6 | 8.5 | 8.7 | 8.7 |
| pH at DV 10 | 8.5 | 4 | 8.6 | 8.4 | 8.6 | 8.6 |
| Final pH | 8.6 | 8.8 | 8.5 | 8.4 | 8.6 | 8.6 |

Table 3 shows conductivity values (ppm) for silk fibroin and lithium bromide solutions during TFF processes:

TABLE 3

CONDUCTIVITY VALUES (PPM) FOR SILK FIBROIN AND LITHIUM BROMIDE SOLUTIONS DURING TFF PROCESSES

|  | Example 6 | Example 9 | Example 10 | Example 11 | Example 12 | Example 13 |
|---|---|---|---|---|---|---|
| Cond. at DV 3 | Over Limit | Over Limit | Over Limit | Over Limit | Over Limit | Over Limit |
| Cond. at DV 4 | 2020 | 1670 | 1900 | 2290 | Over Limit | 2460 |
| Cond. at DV 5 | 830 | 730 | 760 | 950 | Over Limit | 1050 |
| Cond. at DV 6 | 420 | 720 | Over Limit | 740 | Over Limit | 460 |
| Cond. at DV 7 | 410 | 280 | Over Limit | 460 | 1440 | 230 |
| Cond. at DV 8 | 400 | 130 | Over Limit | 430 | 700 | 540 |
| Cond. at DV 9 | 380 | 60 | Over Limit | 430 | 500 | 480 |
| Cond. at DV 10 | 380 | 40 | Over Limit | 410 | 470 | 490 |
| Final Cond. | 560 | 810 | Over Limit | 630 | 690 | 710 |

Table 4 shows permeate flux values (LMH) values during TFF processes:

TABLE 4

PERMEATE FLUX VALUES (LMH) VALUES DURING TFF PROCESSES

|  | Example 6 | Example 9 | Example 10 | Example 11 | Example 12 | Example 13 |
|---|---|---|---|---|---|---|
| Flux at DV 1 | 14.13 | 14.68 | 14.96 | 14.96 | 14.68 | 14.40 |
| Flux at DV 2 | 15.90 | 14.96 | 14.68 | 15.57 | 15.90 | 14.13 |
| Flux at DV 3 | 16.24 | 15.57 | 15.57 | 16.24 | 15.90 | 16.24 |
| Flux at DV 4 | 16.24 | 16.24 | 15.90 | 16.75 | 16.59 | 17.34 |
| Flux at DV 5 | 16.59 | 15.57 | 14.40 | 15.57 | 16.24 | 17.34 |
| Flux at DV 6 | 14.96 | 16.24 | 16.24 | 15.90 | 16.24 | 16.96 |
| Flux at DV 7 | 14.13 | 15.57 | 16.96 | 14.40 | 16.96 | 16.59 |
| Flux at DV 8 | 12.72 | 16.59 | 16.59 | 13.16 | 16.59 | 14.96 |
| Flux at DV 9 | 13.16 | 16.24 | 17.34 | 13.16 | 14.96 | 13.63 |
| Flux at DV 10 | 13.63 | 16.59 | 16.96 | 13.39 | 13.63 | 13.16 |

Table 5 shows permeate flux data from Table 4 represented as change from the control batch of Example 6 at each diavolume:

TABLE 5

PERMEATE FLUX DATA FROM TABLE 4 REPRESENTED AS CHANGE FROM THE CONTROL BATCH OF EXAMPLE 6 AT EACH DIAVOLUME

|  | Example 6 | Example 9 | Example 10 | Example 11 | Example 12 | Example 13 |
|---|---|---|---|---|---|---|
| Flux at DV 1 | — | 3.89% | 5.87% | 5.87% | 3.89% | 1.91% |
| Flux at DV 2 | — | -5.91% | -7.67% | -2.08% | 0.00% | -11.13% |
| Flux at DV 3 | — | -4.13% | -4.13% | 0.00% | -2.09% | 0.00% |
| Flux at DV 4 | — | 0.00% | -2.09% | 3.14% | 2.16% | 6.77% |
| Flux at DV 5 | — | -6.15% | -13.20% | -6.15% | -2.11% | 4.52% |
| Flux at DV 6 | — | 8.56% | 8.56% | 6.28% | 8.56% | 13.37% |
| Flux at DV 7 | — | 10.19% | 20.03% | 1.91% | 20.03% | 17.41% |
| Flux at DV 8 | — | 30.42% | 30.42% | 3.46% | 30.42% | 17.61% |
| Flux at DV 9 | — | 23.40% | 31.76% | 0.00% | 13.68% | 3.57% |
| Flux at DV 10 | — | 21.72% | 24.43% | -1.76% | 0.00% | -3.45% |

Tables 4 and 5 reference the flux (in liters per $m^2$ membrane surface area per hour, or LMH) at each diavolume, measured over the half-diavolume leading up to the time the necessary mass is reached. Table 5 shows the percent increase or decrease when compared to the control run (Example 6). Examples 9, 10, 12, and 13 all showed increases of 10% or greater in various diavolumes, either directly connected to the newer methods or after the fact. In a standard, 10-diavolume process against DI water, there is a steady drop in flux after DV 5 until the end of the run. If, after beginning the process the same way, the pH is reduced or sodium chloride is introduced, this drop in flux can be avoided. In addition to the improvement in reduction of elemental impurities, this is the secondary benefit of these methods.

The improvement in flux is similar between both pH reduction and sodium chloride replacement methods when they are used at the end or in the middle of the run. However, Example 11 and Example 12 show variability in these results. Example 11 shows no improvement in flux over the course of the run, perhaps because the material was adjusted to pH 4 prior to the initial concentration step. Example 12 shows that the increase in flux was during diavolumes 6, 7, 8, and 9, but had returned to a lower value by diavolume 10. In this run, sodium chloride was used as a replacement in the first five diavolumes and then DI water was used. There was no increase in flux in the diavolumes when sodium chloride was used. This indicates the flux is highest when the majority of lithium and bromine has been removed, but the running solution still contains at least some sodium and chloride. As that is removed, and the solution returns to only silk fibroin in water, the flux is again decreased towards the values in the control run.

There is another phenomenon observed during the pH 4 TFF process that further establishes the novelty and unexpected nature of these results Immediately after adjusting the pH of the silk fibroin solution to 4, the solution becomes hazy. This haziness begins to appear around pH 5-6 and persists while the value is maintained at 4. Without being held to theory it is believed that this haziness represents silk fibroin molecules becoming insoluble and coming out of solution. In Example 7, the haziness grew more pronounced from DV 5 to DV 10. This insolubility, importantly, is reversible. Once the pH is adjusted back up towards 7-9 the particulates all go back into solution. This can be observed in Table 3, in Example 7. The conductivity decreases from DV 5 to DV 10 continuously, while the pH is maintained at 4 and the solution is hazy. This is because the elemental impurities are being filtered out and the silk fibroin has precipitated and is no longer registering as being soluble. When the solution is pH adjusted back to above 8.5, the conductivity increases towards that of the other batches, indicating that the silk fibroin has completely returned back into solution. This effect can also be seen in the transition between DV 7 and 8 in Example 13, where the conductivity increases after pH adjustment (this is a combination of the introduction of sodium hydroxide and the solubilization of the silk fibroin). This haziness, counterintuitively, leads to both more efficient reduction in lithium as well as increased flux.

Without being held to theory it is believed that this reversible insolubility is important for reducing the amount of bromine in the solution. This is evident in the fact that the sodium chloride method does not result in this haziness, and also leads to a slight increase in bromine. The standard method of replacement with water at a high pH is relatively effective at removing bromine, but there is improvement in the runs with a lowered pH section. It was also shown, in Table 1, that when these new methods are employed over the entirety of a run (of 7 diavolumes), the bromine levels increased compared to the control batch either 19.0-fold (sodium chloride replacement) or 20.2-fold (pH 4). They were also accompanied by a reduction in lithium at either 5.3-fold (sodium chloride replacement) or 18.4-fold (pH 4).

This method of either reversible precipitation via pH change or preferential elemental exchange using a sodium chloride solution or equivalent is also feasible with other chaotropic agents that can dissolve solid silk fibroin. These can include, but are not limited to, lithium bromide, lithium chloride, calcium chloride, ethanol, guanidinium chloride, or urea. If these compounds help to solubilize the silk fibroin after degumming, it is possible that the methods described here could impact the elemental impurity content of the final silk solution in similar ways. The flux increase from the methods described here could also be reproduced, as that appears to be most prevalent during the end of the run when most of the chaotropic agent would be removed in any case. Therefore, the increased flux as a result of the pH change or the addition of a sodium chloride solution would likely be repeatable even with a different dissolution agent.

Additionally, as a result of reduced calcium impurity in the silk solution after dissolution with the calcium chloride and ethanol mixture, formulation with phosphate containing buffers and solutions is now possible. Previously, after standard dialysis procedures, too much calcium remained and calcium phosphate would precipitate after formulation, making stability and regulation of the material impossible. After these improved processes, however, the calcium was lowered to an extent at which formulation in phosphate-buffered saline was possible without demonstrable precipitation. This would greatly increase the silk material's usefulness and applicability in biomedical applications.

It is therefore shown that there is an improvement for increasing the efficiency of TFF for purifying a silk fibroin solution through the introduction of a salt solution into the replacement feed in the TFF process.

It is also shown that a change in the pH in a very particular and unexpected manner of the retentate silk fibroin solution will also improve the efficiency of the TFF filtration process.

The introduction of the salt solution and the pH change may also be combined to improve the efficiency of the TFF process.

The new TFF process described here also allows for the silk fibroin solution to be reversibly precipitated which allows for increased elemental exchange and improved TFF permeate flux. The TFF flux may be increased by 5 percent or greater over one or more diavolumes with the new process.

The new TFF process also allows for the final elemental content of one or more of the dissolution or chaotropic agents to be significantly reduced by 5-fold or greater as compared to a traditional method.

Inventive Example 14: TF-137 Processing

SF was first degummed, dissolved, diluted, and filtered as in Example 6. A tangential flow filtration (TFF) system with a single 0.11 m² Pellicon® 3 cassette with an Ultracel® 5 kDa membrane was used for removal of lithium bromide. Prior to introduction of SF to the system, the system was washed with DI water and sanitized with 0.1 N sodium hydroxide. The system was then flushed with water to remove sodium hydroxide. All TFF using the 0.11 m² membrane was run at with a flow rate of 4 LMM (liters/m² membrane area/minute).

Using the TFF system, the solution was concentrated from 5% (w/v) to 10% (w/v) SF. Continuous diafiltration was performed at 10% (w/v) SF to remove lithium bromide. The silk fibroin was diafiltered for 10 diavolumes with a replacement feed of DI water. The solution was then concentrated to half of its diafiltration volume and collected. Following TFF, the solution was stored at 4° C. until elemental analysis was completed.

Inventive Example 15: TF-140 Processing

SF was first degummed, dissolved, diluted, and filtered as in Example 6. The TFF system as the same as in Example 14.

Using the TFF system, the solution was concentrated from 5% (w/v) to 10% (w/v) SF. Continuous diafiltration was performed at 10% (w/v) SF to remove lithium bromide. The silk fibroin was diafiltered for 10 diavolumes with a replacement feed of DI water. After the fifth diavolume, the silk fibroin solution was quickly adjusted to pH 2 using hydrochloric acid. The silk fibroin was then diafiltered for the final 5 diavolumes while maintaining a pH of 2. The solution was then concentrated to half of its diafiltration volume and collected. Following TFF, the solution was adjusted back to a pH between 8.5 and 9.0 using sodium hydroxide and stored at 4° C. until elemental analysis was completed.

Inventive Example 16: TF-139 Processing

SF was first degummed, dissolved, diluted, and filtered as in Example 6. The TFF system as the same as in Example 14.

Using the TFF system, the solution was concentrated from 5% (w/v) to 10% (w/v) SF. Continuous diafiltration was performed at 10% (w/v) SF to remove lithium bromide. The silk fibroin was diafiltered for 10 diavolumes with a replacement feed of DI water. After the fifth diavolume, the silk fibroin solution was quickly adjusted to pH 3 using hydrochloric acid. The silk fibroin was then diafiltered for the final 5 diavolumes while maintaining a pH of 3. The solution was then concentrated to half of its diafiltration volume and collected. Following TFF, the solution was adjusted back to a pH between 8.5 and 9.0 using sodium hydroxide and stored at 4° C. until elemental analysis was completed.

Inventive Example 17: TF-138 Processing

SF was first degummed, dissolved, diluted, and filtered as in Example 6. The TFF system as the same as in Example 14.

Using the TFF system, the solution was concentrated from 5% (w/v) to 10% (w/v) SF. Continuous diafiltration was performed at 10% (w/v) SF to remove lithium bromide. The silk fibroin was diafiltered for 10 diavolumes with a replacement feed of DI water. After the fifth diavolume, the silk fibroin solution was quickly adjusted to pH 4 using hydrochloric acid. The silk fibroin was then diafiltered for the final 5 diavolumes while maintaining a pH of 4. The solution was then concentrated to half of its diafiltration volume and collected. Following TFF, the solution was adjusted back to a pH between 8.5 and 9.0 using sodium hydroxide and stored at 4° C. until elemental analysis was completed.

Inventive Example 18: TF-141 Processing

SF was first degummed, dissolved, diluted, and filtered as in Example 6. The TFF system as the same as in Example 14.

Using the TFF system, the solution was concentrated from 5% (w/v) to 10% (w/v) SF. Continuous diafiltration was performed at 10% (w/v) SF to remove lithium bromide. The silk fibroin was diafiltered for 10 diavolumes with a replacement feed of DI water. After the fifth diavolume, the silk fibroin solution was quickly adjusted to pH 5 using hydrochloric acid. The silk fibroin was then diafiltered for the final 5 diavolumes while maintaining a pH of 5. The solution was then concentrated to half of its diafiltration volume and collected. Following TFF, the solution was adjusted back to a pH between 8.5 and 9.0 using sodium hydroxide and stored at 4° C. until elemental analysis was completed.

Inventive Example 19: TF-142 Processing

SF was first degummed, dissolved, diluted, and filtered as in Example 6. The TFF system as the same as in Example 14.

Using the TFF system, the solution was concentrated from 5% (w/v) to 10% (w/v) SF. Continuous diafiltration was performed at 10% (w/v) SF to remove lithium bromide. The silk fibroin was diafiltered for 10 diavolumes with a replacement feed of DI water. After the fifth diavolume, the silk fibroin solution was quickly adjusted to pH 6 using hydrochloric acid. The silk fibroin was then diafiltered for the final 5 diavolumes while maintaining a pH of 6. The solution was then concentrated to half of its diafiltration volume and collected. Following TFF, the solution was adjusted back to a pH between 8.5 and 9.0 using sodium hydroxide and stored at 4° C. until elemental analysis was completed.

Inventive Example 20: TF-143 Processing

SF was first degummed, dissolved, diluted, and filtered as in Example 6. The TFF system as the same as in Example 14.

Using the TFF system, the solution was concentrated from 5% (w/v) to 10% (w/v) SF. Continuous diafiltration was performed at 10% (w/v) SF to remove lithium bromide. The silk fibroin was diafiltered for 10 diavolumes with a replacement feed of DI water. After the fifth diavolume, the silk fibroin solution was quickly adjusted to pH 7 using hydrochloric acid. The silk fibroin was then diafiltered for the final 5 diavolumes while maintaining a pH of 7. The solution was then concentrated to half of its diafiltration volume and collected. Following TFF, the solution was adjusted back to a pH between 8.5 and 9.0 using sodium hydroxide and stored at 4° C. until elemental analysis was completed.

Inventive Example 21: TF-145 Processing

SF was first degummed, dissolved, diluted, and filtered as in Example 6. The TFF system as the same as in Example 14.

Using the TFF system, the solution was concentrated from 5% (w/v) to 10% (w/v) SF. Continuous diafiltration was performed at 10% (w/v) SF to remove lithium bromide. The silk fibroin was diafiltered for 10 diavolumes with a replacement feed of DI water. After the third diavolume, the silk fibroin solution was quickly adjusted to pH 4 using hydrochloric acid. The silk fibroin was then diafiltered for the final 7 diavolumes while maintaining a pH of 4. The solution was then concentrated to half of its diafiltration volume and collected. Following TFF, the solution was adjusted back to a pH between 8.5 and 9.0 using sodium hydroxide and stored at 4° C. until elemental analysis was completed.

Inventive Example 22: TF-144 Processing

SF was first degummed, dissolved, diluted, and filtered as in Example 6. The TFF system as the same as in Example 14.

Using the TFF system, the solution was concentrated from 5% (w/v) to 10% (w/v) SF. Continuous diafiltration was performed at 10% (w/v) SF to remove lithium bromide. The silk fibroin was diafiltered for 10 diavolumes with a replacement feed of DI water. After the fourth diavolume, the silk fibroin solution was quickly adjusted to pH 4 using hydrochloric acid. The silk fibroin was then diafiltered for the final 6 diavolumes while maintaining a pH of 4. The solution was then concentrated to half of its diafiltration volume and collected. Following TFF, the solution was adjusted back to a pH between 8.5 and 9.0 using sodium hydroxide and stored at 4° C. until elemental analysis was completed.

Inventive Example 23: TF-146 Processing

SF was first degummed, dissolved, diluted, and filtered as in Example 6. The TFF system as the same as in Example 14.

Using the TFF system, the solution was concentrated from 5% (w/v) to 10% (w/v) SF. Continuous diafiltration was performed at 10% (w/v) SF to remove lithium bromide. The silk fibroin was diafiltered for 10 diavolumes with a replacement feed of DI water. After the sixth diavolume, the silk fibroin solution was quickly adjusted to pH 4 using hydrochloric acid. The silk fibroin was then diafiltered for the final 4 diavolumes while maintaining a pH of 4. The solution was then concentrated to half of its diafiltration volume and collected. Following TFF, the solution was adjusted back to a pH between 8.5 and 9.0 using sodium hydroxide and stored at 4° C. until elemental analysis was completed.

Inventive Example 24: TF-147 Processing

SF was first degummed, dissolved, diluted, and filtered as in Example 6. The TFF system as the same as in Example 14.

Using the TFF system, the solution was concentrated from 5% (w/v) to 10% (w/v) SF. Continuous diafiltration was performed at 10% (w/v) SF to remove lithium bromide. The silk fibroin was diafiltered for 10 diavolumes with a replacement feed of DI water. After the seventh diavolume, the silk fibroin solution was quickly adjusted to pH 4 using hydrochloric acid. The silk fibroin was then diafiltered for the final 3 diavolumes while maintaining a pH of 4. The solution was then concentrated to half of its diafiltration volume and collected. Following TFF, the solution was adjusted back to a pH between 8.5 and 9.0 using sodium hydroxide and stored at 4° C. until elemental analysis was completed.

Inventive Example 25: TF-148 Processing

SF was first degummed, dissolved, diluted, and filtered as in Example 6. The TFF system as the same as in Example 14.

Using the TFF system, the solution was concentrated from 5% (w/v) to 10% (w/v) SF. Continuous diafiltration was performed at 10% (w/v) SF to remove lithium bromide. The silk fibroin was first diafiltered for 5 diavolumes with a replacement feed of DI water. The silk fibroin was then diafiltered for 5 additional volumes with a replacement feed of 150 mM sodium chloride solution, for a total of 10 diavolumes. The solution was then concentrated to half of its diafiltration volume and collected. Following TFF, the solution was stored at 4° C. until elemental analysis was completed.

Inventive Example 26: TF-149 Processing

SF was first degummed, dissolved, diluted, and filtered as in Example 6. The TFF system as the same as in Example 14.

Using the TFF system, the solution was concentrated from 5% (w/v) to 10% (w/v) SF. Continuous diafiltration was performed at 10% (w/v) SF to remove lithium bromide. The silk fibroin was first diafiltered for 5 diavolumes with a replacement feed of DI water. The silk fibroin was then diafiltered for 5 additional volumes with a replacement feed of 150 mM calcium chloride solution, for a total of 10 diavolumes. The solution was then concentrated to half of its diafiltration volume and collected. Following TFF, the solution was stored at 4° C. until elemental analysis was completed.

Inventive Example 27: TF-150 Processing

SF was first degummed, dissolved, diluted, and filtered as in Example 6. The TFF system as the same as in Example 14.

Using the TFF system, the solution was concentrated from 5% (w/v) to 10% (w/v) SF. Continuous diafiltration was performed at 10% (w/v) SF to remove lithium bromide. The silk fibroin was first diafiltered for 5 diavolumes with a replacement feed of DI water. The silk fibroin was then diafiltered for 5 additional volumes with a replacement feed of 150 mM calcium chloride solution, for a total of 10 diavolumes. After the fifth diavolume, the silk fibroin solution was adjusted to pH 4 using hydrochloric acid. The pH was maintained at 4 through the final five diavolumes against calcium chloride. The solution was then concentrated to half of its diafiltration volume and collected. Following TFF, the solution was adjusted back to a pH of 8.5 to 9.0 using sodium hydroxide and stored at 4° C. until elemental analysis was completed.

Inventive Example 28: TF-151 Processing

SF was first degummed, dissolved, diluted, and filtered as in Example 6. The TFF system as the same as in Example 14.

Using the TFF system, the solution was concentrated from 5% (w/v) to 10% (w/v) SF. Continuous diafiltration was performed at 10% (w/v) SF to remove lithium bromide. The silk fibroin was first diafiltered for 5 diavolumes with a replacement feed of DI water. The silk fibroin was then diafiltered for 5 additional volumes with a replacement feed of 150 mM magnesium chloride solution, for a total of 10 diavolumes. The solution was then concentrated to half of its diafiltration volume and collected. Following TFF, the solution was stored at 4° C. until elemental analysis was completed.

TABLE 6

RESULTS FOR EXAMPLES 14-28

| Sample | Replacement Feed | Lithium ppm (mg Li/kg silk fibroin) |
|---|---|---|
| Inventive Example 14 | DI water for diavolumes 1-10 | 1468 |
| Inventive Example 15 | DI water for diavolumes 1-10, silk solution adjusted to pH 2 and maintained at 2 for diavolumes 6-10 | 22 |
| Inventive Example 16 | DI water for diavolumes 1-10, silk solution adjusted to pH 3 and maintained at 3 for diavolumes 6-10 | 19 |
| Inventive Example 17 | DI water for diavolumes 1-10, silk solution adjusted to pH 4 and maintained at 4 for diavolumes 6-10 | 40 |
| Inventive Example 18 | DI water for diavolumes 1-10, silk solution adjusted to pH 5 and maintained at 5 for diavolumes 6-10 | 458 |
| Inventive Example 19 | DI water for diavolumes 1-10, silk solution adjusted to pH 6 and maintained at 6 for diavolumes 6-10 | 805 |
| Inventive Example 20 | DI water for diavolumes 1-10, silk solution adjusted to pH 7 and maintained at 7 for diavolumes 6-10 | 1020 |
| Inventive Example 21 | DI water for diavolumes 1-10, silk solution adjusted to pH 4 and maintained at 4 for diavolumes 4-10 | 28 |
| Inventive Example 22 | DI water for diavolumes 1-10, silk solution adjusted to pH 4 and maintained at 4 for diavolumes 5-10 | 85 |
| Inventive Example 23 | DI water for diavolumes 1-10, silk solution adjusted to pH 4 and maintained at 4 for diavolumes 7-10 | 86 |
| Inventive Example 24 | DI water for diavolumes 1-10, silk solution adjusted to pH 4 and maintained at 4 for diavolumes 8-10 | 68 |
| Inventive Example 25 | DI water for diavolumes 1-5, 150 mM sodium chloride for diavolumes 6-10 | 38 |
| Inventive Example 26 | DI water for diavolumes 1-5, 150 mM calcium chloride for diavolumes 6-10 | 29 |
| Inventive Example 27 | DI water for diavolumes 1-5, 150 mM sodium chloride for diavolumes 6-10, silk solution adjusted to pH 4 and maintained at 4 for diavolumes 6-10 | 25 |
| Inventive Example 28 | DI water for diavolumes 1-5, 150 mM magnesium chloride for diavolumes 6-10 | 30 |

Inventive Examples 14-28 expand upon the parameters of the methods described in Examples 1-13. For Examples 14-37, lithium was determined according to US EPA Method 200.7, Rev. 4.4, "Determination of Metals and Trace Elements in Water and Wastes by Inductively Coupled Plasma-Atomic Emission Spectrometry," and bromide was determined according to US EPA Method 300.0, Rev. 2.1, "Determination of Inorganic Anions by Ion Chromatography." Calcium was determined for Examples 29-31 in a similar manner to lithium in Examples 1-13.

Examples 14-28 focused solely on lithium as it is a more relevant impurity to prove the safety of a silk fibroin ingredient. Example 14 provided a control group of diafiltering silk fibroin solution with a replacement feed of water with no alteration to the retentate. Examples 15-20 show a range of pH values for the retentate. In each case, the solution was diafiltered for 5 diavolumes with an unaltered pH, before the pH was lowered for the remaining 5 diavolumes. The pH values include 2, 3, 4, 5, 6, and 7. The fold-decrease in lithium for each pH value are 67×, 77×, 37×, 3.2×, 1.8×, and 1.4×, respectively. There is a drastic change in the efficacy of the method between pH values of 4 and 5. This corresponds to the reported isoelectric point of silk fibroin (typically listed as 4.0-4.5). Without being held to theory, when silk fibroin retentate solution is below its isoelectric point, it seems to preferentially release the cationic lithium, but when above its isoelectric point, it seems to preferentially release the anionic bromine. This would potentially explain why standard dialysis methods have much more lithium than bromine, as silk fibroin typically is slightly basic in solution. Therefore, the most ideal processing method to reduce elemental impurities would need to include diafiltration or dialysis time on both sides of silk fibroin's isoelectric point.

Examples 21-24 expand upon when the pH change is introduced during diafiltration. pH 4 was chosen as the ideal pH. The pH change was introduced after 3, 4, 5 (Example 17), 6, and 7 diavolumes at the unaltered, higher pH of 8.5-9.0. In contrast to the control, each run showed similarly reduced lithium content. Any of these would be viable options for an improved TFF process with regards to lithium reduction. The timing of the pH change may impact bromine levels.

Examples 25-28 examine different replacement feeds. These include 150 mM sodium chloride solution, 150 mM calcium chloride solution, and 150 mM magnesium chloride solution. All of these solutions were introduced halfway through the diafiltration, after 5 diavolumes with a pure water replacement feed. Additionally, as shown in Example 27, the calcium chloride replacement feed was combined with the retentate pH change to 4 to determine if any synergistic effects exist. There does not appear to be any drastic difference in the amount of lithium reduction across these groups. All showed reduction similar to, or greater than, that shown by the pH alteration methods. All of these salts are viable options to improve the TFF process, and it is reasonable to assume other like salts can be used just as effectively.

Inventive Example 29: TF-132 Processing

SF was first degummed as in Example 6. To dissolve the degummed SF fibers, 500 g of the degummed SF was placed in a 1-gallon glass jar along with 2 L of Ajisawa's reagent. Ajisawa's reagent is a solution consisting of a 1:2:8 molar ratio of calcium chloride to ethanol to water, respectively. The jar was incubated at 80° C. overnight to dissolve the SF fibers. Prior to tangential flow filtration, the silk fibroin solution was diluted from 20% (w/v) SF to 5% (w/v) SF with DI water. The diluted solution was then filtered through an approximately 5 μm cellulose membrane to remove any remaining particulates. The TFF system was the same as in Example 6.

Using the TFF system, the solution was concentrated from 5% (w/v) to 10% (w/v) SF. Continuous diafiltration was performed at 10% (w/v) SF to remove lithium bromide. The silk fibroin was diafiltered for a total of 10 diavolumes with a replacement feed of DI water. The solution was then concentrated to half of its diafiltration volume and collected. Following TFF, the solution was filtered through an approximately 1 μm cellulose filter and stored at 4° C. until elemental analysis was completed.

Inventive Example 30: TF-134 Processing

SF was first degummed as in Example 6. To dissolve the degummed SF fibers, 350 g of the degummed SF was placed in a 1-gallon glass jar along with 3.15 L of Ajisawa's reagent. Ajisawa's reagent is a solution consisting of a 1:2:8 molar ratio of calcium chloride to ethanol to water, respectively. The jar was incubated at 80° C. for 2 hours to dissolve the SF fibers. Prior to tangential flow filtration, the silk fibroin solution was diluted from 10% (w/v) SF to 5% (w/v) SF with DI water. The diluted solution was then filtered through an approximately 5 μm cellulose membrane to remove any remaining particulates. The TFF system was the same as in Example 6.

Using the TFF system, the solution was concentrated from 5% (w/v) to 10% (w/v) SF. Continuous diafiltration was performed at 10% (w/v) SF to remove lithium bromide. The silk fibroin was diafiltered for a total of 10 diavolumes with a replacement feed of DI water. After the fibroin was diafiltered for a total of 10 diavolumes with a replacement feed of DI water. After the fifth diavolume, the silk fibroin feed solution was quickly adjusted to pH 4 using hydrochloric acid. The remaining diavolumes were completed while maintaining a pH of 4. The solution was then concentrated to half of its diafiltration volume and collected. Following TFF, the solution was adjusted back to a pH between 8.5 and 9.0 using sodium hydroxide and filtered through an approximately 1 μm cellulose filter and stored at 4° C. until elemental analysis was completed.

Inventive Example 31: TF-135 Processing

SF was first degummed as in Example 6. The SF was dissolved and filtered as in Example 15. The TFF system was the same as in Example 6.

Using the TFF system, the solution was concentrated from 5% (w/v) to 10% (w/v) SF. Continuous diafiltration was performed at 10% (w/v) SF to remove lithium bromide. The silk fibroin was first diafiltered for a total of 5 diavolumes with a replacement feed of DI water, and then diafiltered for an additional 5 diavolumes (10 total) with a replacement feed of 150 mM sodium chloride solution in water. The solution was then concentrated to half of its diafiltration volume and collected. Following TFF, the solution was filtered through an approximately 1 μm cellulose filter and stored at 4° C. until elemental analysis was completed.

TABLE 7

RESULTS FOR EXAMPLES 29-31

| Sample | Replacement Feed | Calcium ppm (mg Ca/kg silk fibroin) |
| --- | --- | --- |
| Inventive Example 29 | DI water for diavolumes 1-10 | 4288 |
| Inventive Example 30 | DI water for diavolumes 1-10, silk solution adjusted to pH 4 and maintained at 4 for diavolumes 6-10 | 72 |
| Inventive Example 31 | DI water for diavolumes 1-5, 150 mM sodium chloride for diavolumes 6-10 | 371 |

Examples 29-31 demonstrate the applicability of these processes with chaotropic agents beyond lithium bromide.

In this case, a mixture of calcium chloride, ethanol, and water was used. Example 29 was the standard TFF method, with no alteration to the retentate and a pure water replacement feed. Example 30 involved lowering the pH of the retentate to 4 halfway through diafiltration, and Example 31 involved switching to a sodium chloride replacement feed halfway through diafiltration. Example 30 resulted in a 60× reduction in calcium, and Example 31 resulted in a 12× reduction in calcium. The pH method appears to be similarly useful in reducing cationic content with this dissolution agent, with the salt solution replacement feed being less drastic, but still sufficient to allow for the benefits referenced earlier.

Comparative Example 32: DSC-SC-20 Processing
(Degumming Similar to WO 2020/247594,
Example 34; Desalting as in Rockwood et al.)

Silk fibroin was prepared by degumming silk yarn in a sodium carbonate solution, dissolving in lithium bromide, and purifying via dialysis. 31.3 L of water and 1.66 kg of sodium carbonate (0.5 M sodium carbonate) were added to a vessel and heated to 85° C. 2.5 kg of silk yarn was added to the solution. The silk yarn was degummed for 4 hours at After 4 hours, the silk yarn was removed and rinsed under DI water to remove excess carbonate solution. The fibroin fibers were then squeezed to remove water and spread in a oven to dry over two days.

After drying, 30 g of the silk fibroin was packed into a 250 mL bottle and 120 mL of 9.3 M lithium bromide was added. The bottle was capped and allowed to heat at 60° C. overnight (around 20 hours). The resulting 20% (w/v) silk fibroin solution in lithium bromide was then poured into 3.5 kDa dialysis cassettes and placed into 5 L of DI water under stirring to dialyze. The water was completely exchanged 6 times over the next 48 hours. After dialysis, the solution was combined, centrifuged for 20 minutes at 10000×g to remove any insoluble particulates, and stored at 4° C. prior to analysis.

Inventive Example 33: DSC-SC-21 Processing

Silk fibroin was degummed and dried as in Example 32.
After drying, 30 g of the silk fibroin was packed into a 250 mL bottle and 120 mL of 9.3 M lithium bromide was added. The bottle was capped and allowed to heat at 60° C. overnight (around 20 hours). A portion was diluted 1:1 with DI water first, and then the resulting 10% (w/v) silk fibroin solution was poured into 3.5 kDa dialysis cassettes and placed into 5 L of DI water under stirring to dialyze. A portion was diluted 1:3 with DI water first, and then the resulting 5% (w/v) silk fibroin solution was poured into 3.5 kDa dialysis cassettes and placed into 5 L of DI water under stirring to dialyze. A portion was diluted 1:19 with DI water first, and then the resulting 1% (w/v) silk fibroin solution was poured into 3.5 kDa dialysis cassettes and placed into 5 L of DI water under stirring to dialyze. The water was completely exchanged 6 times over the next 48 hours. After dialysis, each solution was combined, centrifuged for 20 minutes at 10000×g to remove any insoluble particulates, and stored at 4° C. prior to analysis.

Inventive Example 34: DSC-SC-22 Processing

Silk fibroin was degummed and dried as in Example 32.
After drying, 30 g of the silk fibroin was packed into a 250 mL bottle and 120 mL of 9.3 M lithium bromide was added. The bottle was capped and allowed to heat at 60° C. overnight (around 20 hours). The resulting 20% (w/v) silk fibroin solution in lithium bromide was then poured into 3.5 kDa dialysis cassettes and placed into 5 L of DI water under stirring to dialyze. The water was completely exchanged 6 times over the next 48 hours. After the third exchange (approximately 24 hours after beginning dialysis), the silk fibroin solution was removed from the cassettes, combined, adjusted to pH 4 using hydrochloric acid, and then returned to the cassettes for dialysis. At each subsequent water change through the sixth, the solution was removed and the pH was adjusted to 4 if necessary. After dialysis, the solution was combined, pH-adjusted back to between 8.5 and 9.0 using sodium hydroxide, centrifuged for 20 minutes at 10000×g to remove any insoluble particulates, and stored at 4° C. prior to analysis.

Inventive Example 35: DSC-SC-23 Processing

Silk fibroin was degummed and dried as in Example 32.
After drying, 30 g of the silk fibroin was packed into a 250 mL bottle and 120 mL of 9.3 M lithium bromide was added. The bottle was capped and allowed to heat at 60° C. overnight (around 20 hours). The resulting 20% (w/v) silk fibroin solution in lithium bromide was then pH adjusted to 4 using hydrochloric acid, poured into 3.5 kDa dialysis cassettes, and placed into 5 L of DI water under stirring to dialyze. The water was completely exchanged 6 times over the next 48 hours. At each water change the silk fibroin solution was removed and the pH was adjusted to 4 if necessary before returning it to the cassettes. After dialysis, the solution was combined, pH-adjusted back to between 8.5 and 9.0 using sodium hydroxide, centrifuged for 20 minutes at 10000×g to remove any insoluble particulates, and stored at 4° C. prior to analysis.

Inventive Example 36: DSC-SC-24 Processing

Silk fibroin was degummed and dried as in Example 32.
After drying, 30 g of the silk fibroin was packed into a 250 mL bottle and 120 mL of 9.3 M lithium bromide was added. The bottle was capped and allowed to heat at 60° C. overnight (around 20 hours). The resulting 20% (w/v) silk fibroin solution in lithium bromide was then poured into 3.5 kDa dialysis cassettes and placed into 5 L of DI water under stirring to dialyze. The water was completely exchanged 6 times over the next 48 hours. After the third exchange, the dialysis buffer was changed from DI water to 150 mM sodium chloride in water. This remained the dialysis buffer through the final exchange. After dialysis, the solution was combined, centrifuged for 20 minutes at 10000×g to remove any insoluble particulates, and stored at 4° C. prior to analysis.

Inventive Example 37: DSC-SC-25 Processing

Silk fibroin was degummed and dried as in Example 32.
After drying, 30 g of the silk fibroin was packed into a 250 mL bottle and 120 mL of 9.3 M lithium bromide was added. The bottle was capped and allowed to heat at 60° C. overnight (around 20 hours). The resulting 20% (w/v) silk fibroin solution in lithium bromide was then poured into 3.5 kDa dialysis cassettes and placed into 5 L of 150 mM sodium chloride solution under stirring to dialyze. The same salt solution was completely exchanged 6 times over the next 48 hours. After dialysis, the solution was combined, centrifuged for 20 minutes at 10000×g to remove any insoluble particulates, and stored at 4° C. prior to analysis.

TABLE 8

RESULTS FOR EXAMPLES 32-37

| Sample | Replacement Feed | Lithium ppm (mg Li/kg silk fibroin) | Bromine ppm (mg Br/kg silk fibroin) |
|---|---|---|---|
| Comparative Example 32 | Dialysis against water for 6 changes | 1638 | 32 |
| Inventive Example 33 (10%) | Dialysis against water for 6 changes at 10% SF | 1492 | 34 |
| Inventive Example 33 (5%) | Dialysis against water for 6 changes at 5% SF | 1472 | 85 |
| Inventive Example 33 (1%) | Dialysis against water for 6 changes at 1% SF | 1275 | 174 |
| Inventive Example 34 | Dialysis against water for 6 changes, with SF at pH 4 for changes 4-6 | 120 | 54 |
| Inventive Example 35 | Dialysis against water for 6 changes, with SF at pH 4 for all changes | 4.7 ppm* | 6.1 ppm* |
| Inventive Example 36 | Dialysis against water for changes 1-3, dialysis against 150 mM sodium chloride in water for changes 4-6 | 89 | 21 |
| Inventive Example 37 | Dialysis against 150 mM sodium chloride in water for 6 changes | 97 | 28 |

*= not normalized to silk fibroin concentration, as concentration could not be determined accurately. Results listed are the concentrations in silk solution. However, these results align with Examples 34, 36, and 37, and it is reasonable to assume that the concentration of silk fibroin is similar to those groups.

Examples 32-37 demonstrate the applicability of these methods using dialysis to exchange the chaotropic salts. Example 32 is the standard method described in the art, wherein silk fibroin solution in lithium bromide is placed into a dialysis cassette with a 3.5 kDa membrane and dialyzed against pure water for 48 hours with 6 complete water exchanges. Example 33 determined that the starting concentration of silk fibroin in lithium bromide has no impact on elemental impurity content after dialysis. Example 34 replicated the TFF method above by changing the silk fibroin solution pH to 4 after 3 exchanges and 24 hours, and then maintaining that pH until dialysis was complete. This led to a 14× reduction in lithium, which while not as drastic as the TFF methods, does demonstrate that the effect carries into this salt exchange methodology. Example 35 was run with the silk fibroin solution at pH 4 for the entire 48 hours. This material demonstrated similar elemental impurity results, but due to gelation an accurate silk fibroin concentration could not be determined for normalization.

Examples 36 and 37 mimicked the salt replacement method by placing the dialysis cassettes in excess 150 mM sodium chloride solution as opposed to water for either the second half of dialysis or the entirety of it, respectively. These both showed similar lithium reduction levels of 18× and 17×, respectively, while maintaining low bromine. This is an important distinction from the TFF methods, where if the salt replacement feed was maintained for an entire run, the bromine levels would elevate (see Example 7.) Without being held to theory, this difference could be related to the mechanical apparatus needed for TFF, to the different chemical environments of a pressured TFF as opposed to a static dialysis, or because of the time differential between a several hour TFF and a two-day dialysis.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A method of purifying a silk fibroin preparation, comprising
   preparing an aqueous silk fibroin solution having a concentration of greater than or equal to 5% w/v silk fibroin from the silk fibroin preparation, wherein the silk fibroin preparation and aqueous solution comprise a chaotropic salt; and
   exchanging the chaotropic salt from the aqueous silk fibroin solution by continuous diafiltration by tangential flow filtration (TFF) to prepare purified silk fibroin, wherein TFF is done with a solution having a pH below the isoelectric point of the silk fibroin, wherein the pH is between 2 and 5 and the pH is maintained between 2 and 5 during at least a portion of the TFF diafiltration;
   wherein the chaotropic salt is LiBr,
   wherein the silk fibroin preparation was prepared by a process comprising dissolving degummed silk fibroin fibers in 5 M to 13 M LiBr,
   wherein the purified silk fibroin comprises 10 to 600 mg lithium per kg silk fibroin as determined by Inductively Coupled Plasma-Mass Spectrometry (ICP-MS), and wherein the only solvent in the method of purifying is water.

2. The method of claim 1, wherein tangential flow filtration (TFF) is performed with a 5 kDa to 10 kDa molecular weight cut-off membrane.

3. The method of claim 2, wherein, prior to providing the reduced pH TFF solution, the method comprises filtering least 3 diafiltration volumes with a water replacement feed.

4. The method of claim 1, wherein the TFF solution further comprises 10 to 300 mM of a second salt.

5. The method of claim 4, wherein the second salt comprises a Mg, Ca, K, or Na salt.

6. The method of claim 1, further comprising adjusting the pH of the purified silk fibroin preparation to a pH of 7-9.

7. The method of claim 1, further comprising adjusting the pH of the purified silk fibroin preparation to a pH of 8.5-9.

8. The method of claim 1, wherein the silk fibroin preparation is degummed in 0.05 to 1 M sodium carbonate at a temperature of about 60° C. to about 90° C., and for a time of greater than 60 minutes to about 480 minutes, to provide the degummed silk fibers, wherein the degummed silk fibers have a sericin concentration of 0-0.5 wt %.

9. A method of purifying a silk fibroin preparation, comprising
preparing an aqueous silk fibroin solution having a concentration of greater than or equal to 5% w/v silk fibroin from the silk fibroin preparation, wherein the silk fibroin preparation and aqueous solution comprise a chaotropic salt; and
exchanging the chaotropic salt from the aqueous silk fibroin solution using dialysis to prepare purified silk fibroin, wherein the dialysis is at a pH below the isoelectric point of the silk fibroin, wherein the pH is between 2 and 5 and the pH is maintained between 2 and 5 through at least a portion of the dialysis;
wherein the chaotropic salt is LiBr,
wherein the silk fibroin preparation was prepared by a process comprising dissolving degummed silk fibroin fibers in 5 M to 13 M LiBr,
wherein the purified silk fibroin comprises 10 to 600 mg lithium per kg silk fibroin as determined by Inductively Coupled Plasma-Mass Spectrometry (ICP-MS), wherein exchanging the chaotropic salt comprises dialysis, and
wherein the only solvent in the method of purifying is water.

10. The method of claim 9, wherein the dialysis buffer further comprises 10 to 300 mM of a second salt.

11. The method of claim 9, further comprising adjusting the pH of the purified silk fibroin preparation to a pH of 7-9.

12. The method of claim 9, further comprising adjusting the pH of the purified silk fibroin preparation to a pH of 8.5-9.

13. The method of claim 9, wherein the silk fibroin preparation is degummed in 0.05 to 1 M sodium carbonate at a temperature of about 60° C. to about 90° C., and for a time of greater than 60 minutes to about 480 minutes, to provide the degummed silk fibers, wherein the degummed silk fibers have a sericin concentration of 0-0.5 wt %.

* * * * *